United States Patent [19]

Keller et al.

[11] 4,039,286
[45] Aug. 2, 1977

[54] AUTOMATIC CHEMICAL ANALYSIS APPARATUS

[75] Inventors: Walter Keller, Rodenbach II; Hubert Koukol, Bad Nauheim; Werner Ptaschek; Dieter Wendt, both of Bruchkobel, all of Germany

[73] Assignee: W. C. Heraeus GmbH, Hanau am Main, Germany

[21] Appl. No.: 705,916

[22] Filed: July 16, 1976

[51] Int. Cl.² .................... G01N 33/16; G01N 21/24; G01N 1/14
[52] U.S. Cl. .............................. 23/230 R; 23/253 R; 23/259; 141/130
[58] Field of Search ................. 23/230 R, 253 R, 259; 141/130

[56] References Cited

U.S. PATENT DOCUMENTS

| 3,533,744 | 10/1970 | Unger | 23/230 R |
|---|---|---|---|
| 3,644,095 | 2/1972 | Netheler et al. | 23/259 |
| 3,799,744 | 3/1974 | Jones | 23/253 R |
| 3,832,140 | 8/1974 | Lorch et al. | 23/259 |
| 3,854,879 | 12/1974 | Figueroa | 23/230 R |
| 3,883,305 | 5/1975 | Hoskins et al. | 23/259 X |
| 3,883,306 | 5/1975 | Widen | 23/253 R |
| 3,897,216 | 7/1975 | Jones | 23/259 |

FOREIGN PATENT DOCUMENTS

| 1,648,900 | 6/1971 | Germany |
|---|---|---|
| 2,140,555 | 2/1972 | Germany |

*Primary Examiner*—R.E. Serwin
*Attorney, Agent, or Firm*—Flynn & Frishauf

[57] ABSTRACT

To permit flexibility in chemical testing steps, a plurality of automatic chemical apparatus units are arranged in modular form, each unit including a main sample receptacle transport conveyor to move the receptacle holding a sample to be tested in a main transport path, a plurality of test and treatment containers being associated with each unit, and a sampling transfer station is located to extract a sample of test substance from the sample receptacle and introduce it into one of the test and treatment containers, which test and treatment container is then moved in a separate test and treatment conveyor path along a plurality of testing and treatment stations until the entire analysis of the removed sample is completed, at which time a new sample receptacle is moved along the main path to the sampling transfer station for introducing a new sample into a subsequent test and treatment receptacle. Movement, in steps, of the sample receptacle and of the test and treatment containers is synchronized so that, at any one time, only one sample container is present at the sampling transfer station. If a plurality of such modular units are assembled together, the stepping of movement of the sample receptacle past the respective transfer stations of the respective modular units is controlled by the longest time period taken to carry out the analysis steps of any one modular unit, sample receptacles for subsequent tests being held at a sample feeder which supports the receptacles in a sinuous, meandering path for introduction, one at a time, to the analysis units in accordance with the slowest test procedures being carried out, so that errors in identification and coordination of test results with samples are reliably avoided.

15 Claims, 5 Drawing Figures

AUTOMATIC CHEMICAL ANALYSIS APPARATUS

The present invention relates to an automatic chemical multi-analysis apparatus, and more particularly to such an apparatus to test fluids, especially liquids, introduced at a main sampling track, for removal of sampling quantities and specific analysis of the sampling quantities with respect to physical or chemical characteristics thereof.

Various types of automatic chemical analysis apparatus for liquids have been proposed. Modern analysis technology permits many different types of analyses to be performed. Some of these steps take more time than others, or require more physical space for the apparatus. Known types of automatic test apparatus were usually arranged in such a way that a fixed transport conveyor, with fixed openings for sample holders, transported the sample holders in the fixed spacing in repetitive steps. Such systems had the disadvantage that the temporal spacing of the sample holders is given by the physical spacing thereof on the transport conveyor and, as a consequence, if one analysis step required more time than another, the results of the analyses from a specific sample were obtained from various analysis apparatus with different time delays. This greatly complicates allocation of the data obtained with the respective samples and particularly a computer program which evaluates the data, allocates them to a particular sample, and provides a single computerized print-out.

It has also been proposed (see German Disclosure Document 1,805,691) to move sample containers along a row of parallel test probes or the like in order to take a portion of the sample from the container into each test probe and then move the test probe laterally; after a certain period of time, the sample containers are moved and the result of analysis of the sample quantities in the test probes is commonly printed out at one instant. The conveying movement is in steps. A separate transport conveyor moves cards or forms carrying an identification of the particular sample. The sample carrier and the sample analysis results are then photographed together with the particular identification card at the reading station. This system requires much apparatus and is complex and does not permit various types of analysis to be performed of the material contained in the separate probes.

It is an object of the present invention to provide an apparatus which is versatile, permits various types of analyses to be performed on any one sample, so that automatic chemical analysis, and particularly multiple analysis can be carried out taking test samples from a larger sampling quantity in a receptacle, and in which the results of the various types of analysis of any one sample will be provided at the same time, regardless of the time taken by the various analysis steps to be undertaken and to provide for simple and reliable allocation of the results of the analysis with respect to a specific main sample in any one readily identified sample receptacle.

Subject Matter of the Present Invention

Briefly, at least one, but preferably several modular apparatus analysis units are provided; each one of them has a main sample receptacle transport conveyor to hold and move a sample receptacle along a main transport path. Each one of them also has a plurality of test and treatment containers and a test and treatment transport conveyor to hold and move the test and treatment containers along a test and treatment transport path which, preferably, extends parallel to but spaced from the main transport path. A sampling transfer station is provided at each unit, in which a sample of the material, typically a liquid, is removed from the sampling receptacle and introduced into one of the test and treatment containers in the test and treatment path, where the test and treatment container, then, is moved along a plurality of testing and treatment stations which carry out various chemical analysis treatments and tests to determine chemical and physical characteristics of the material in the sample receptacle. A common control unit is provided which is coupled both to the main transport conveyor as well as to the test and treatment transport conveyor to control, in steps, movement of the test and treatment containers past the plurality of testing and treatment stations of the respective units and the dwell time of the test and treatment containers at the station and movement of the sample containers from one unit to the next, the control being so effected that the dwell time and movement occur in steps, with movement of the test and treatment containers from one station to the next being timed to occur at that rate which is required by the slowest one of the test and treatment steps being carried out at any one of said stations at any one of the units, so that the final evaluation of a sample at all of the analysis apparatus units will occur at the same time, at which time also the sample in the sampling receptacle is moved along the main transport conveyor path to the next analysis unit, so that the allocation of test results will be unambiguous and only one sampling receptacle will be at the main transport path of any one unit at any one time.

In accordance with a feature of the invention, the control can be so effected that, upon removal of a sample quantity to be tested at a transfer station, the sampling receptacle is immediately moved to the next apparatus unit for removal, likewise, of a sampling quantity to be analyzed in a test and treatment container of the next unit, stepping of the movement of the test and treatment containers within the various units being, however, controlled by the slowest one of the analysis steps after the last one of the units has removed a sample quantity from the sample receptacle. Removal of sample quantities is rapid and thus the delay in starting the first test is small; the simplification in the resulting allocation, however, of test results with the particular sample from which the material to be tested was removed is simplified.

The system and apparatus of the present invention permit the application of a main sample from a sample receptacle to various test and treatment paths so that the same analysis time for the same sample can be used in all the modular units in which the various types of analyses are carried out.

Any one of the main transport paths, or portions thereof, will, in accordance with a feature of the invention, only have a single receptacle thereon; the stepping rate of the test and treatment containers in the test and treatment paths of the various modular units will, however, maintain the same time for each analysis step (whether needed or not), so that unambiquous and simple allocation of the results of the analyses to the respective sample receptacle from which the sample was derived is ensured, without expensive individual identification of the sample material in any one of the test and treatment containers. This is possible since the sequence of the data, or results of the analyses are equal to the sequence of movement of the sample receptacles on the main conveyor path if only one modular unit is used or of that portion of the conveyor path extending through one of the modular units of the apparatus array if at least two of said units are used. It is thus not necessary to specifically identify the various test and treatment containers in the test and treatment paths being subjected to specific testing steps at any one time, since identification of the particular sample in a sample receptacle can be carried out once before the sample receptacle is introduced into the main transport path of the first unit. A sensing switch is provided at each one of the units to sense introduction of a sample receptacle thereto and then also initiate operation of a sampling transfer by a test and treatment transfer device and to synchronize introduction of sample receptacle with movement of test and treatment conveyors.

The invention will be described by way of example with reference to the accompanying drawings, wherein.

Figure 1:
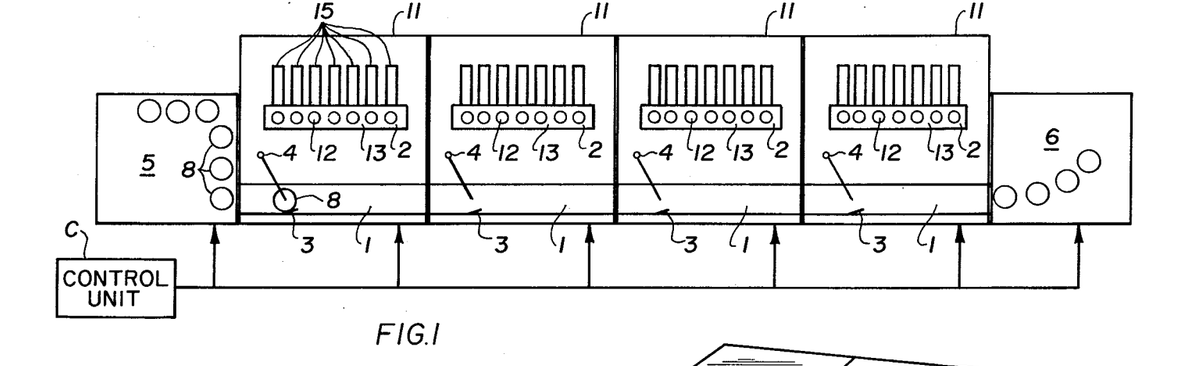
FIG. 1 is a highly schematic view of an array or assembly of modular automatic chemical apparatus units, combined with a feeding system, and showing the general arrangement of the elements.

A plurality of analyzer modules 11 (FIG. 1) are located side-by-side. Main sample receptacles 8 are supplied to a main transport conveyor path 1, where the receptacles 8 are moved along by suitable conveyor means, not shown in FIG. 1, from a sample feeder unit 5, then through the units 11 and from one to the next to a collecting box 6 for used sample receptacles. Each one of the units 11 has, additionally, a test and treatment transport path 2 where a suitable conveyor can move test and treatment containers 12 past analysis stations 15. The main conveyor paths 1 of each one of the units 11 are arranged in alignment. The various analysis units 11 carry out different analysis programs. In the sample of FIG. 1, four such units are shown but any number of units may be assembled, in modular form, with each other. The collecting box merely receives used samples or, additionally, may store them and align them, for example for cleaning and re-use, and may be similar to the sample feeder 5, which will be explained in more detail below.

Each one of the units 11 has a sensing switch 3 at the forward end of the transport path to sense presence of a sample receptacle 8 in the path. A sampling transfer device 4 then is actuated to take a small test sample from the sample receptacle 8 and introduce that test sample into the first one of the analysis or test and treatment containers 12 which is in position for testing and analysis of the material, typically a liquid, in the receptacles 8.

The various modular units 11 are so arranged that the main transport path 1 extends in essentially a straight line, so that the sample containers 8 pass the entire array of automatic analysis units, one by one; each one of the units, further, contains the sample transfer device 4 so that the analysis containers can be charged with samples from the sample receptacles 8 as soon as a sample receptacle 8 is moved, on the main path 1, in cooperative position with respect to the transfer device 4. The sample feeder 5 supplies the sample receptacles 8, one by one, to the main path, and as soon as a first sample container reaches switch 3, the switch 3 of the first sample container will energize the transfer device 4 to take a test sample from the first sample container.

The switch 3 is so associated with operation of the device that it can itself control the transfer device 4. As soon as switch 3 of the first unit 11 is energized, it provides a respective control signal to a central control unit C (FIG. 1) to stop the conveyor beneath path 1. Simultaneously, operation of the switch controls generation of a signal to energize the transfer device 4 and, as soon as a sample quantity has been transferred to a respective container 12, to start the program for analysis of the material within the container 12 and synchronously starting movement of the test and treatment conveyors (step by step). After the transfer of the sample quantity by the transfer device 4, as sensed for example by a reset signal provided by the sampling device 4, the conveyor moving receptacle 8 is again started to move the receptacle 8 to the next subsequent analysis unit 11 where it will stop when the switch 3 is triggered by the sample receptacle 8, and the cycle will repeat. Any number of such analysis units 11, therefore, can be charged with the same sample from the same sample container. Since the transfer device 4 operates rapidly, little time is lost for overall analysis if none of the units 11 commences the first analysis until after all the units 11 have received a sample from the sample receptacle 8 then in the main path 1. This one sample container thus passes through the entire main path 1, that is, past all sequentially located analysis units or modules 11.

The control unit C can be programmed and interlocked with the signals from the switches 3 and, respectively, the reset signal from transfer unit 4 in such a manner that the analysis of the sample removed to a test container 12 from the receptacle 8 of any one unit 11 is started as soon as the sample is transferred into a container 12 of the respective unit 11, and the movement of the test containers 12 past the various analysis steps in the test and treatment path 2 is synchronously started. The output derived from the modules or units 11, that is, the results of the analysis of a test sample taken from the sample receptacle 8 is available at the time the partial samples in the test and treatment containers 12 are analyzed in the various modules. A new sample receptacle 8 is fed from the sample feeder 5 only after the analysis step of one of the modules 11 has been completed. The sequence of introduction of sample receptacles 8 by the sample feeder 5 to the main path is synchronized with the time required during which the test containers for individual analysis in the respective units 11.

Control unit C, therefore, can be programmed, selectively, as desired, in accordance with the required time for the various analyses to be made.

When the last one of the test results is available from the respective units 11, according to the analysis made, then, and only then, is print-out of the result effected. The control of the stepping of the test and analysis containers 12 through the various analysis stations 15 of the various units 11 may well be controlled centrally from the control unit C to commence after the switch 3 has sensed presence of a sample receptacle 8 thereat. This simplifies the program since a comparison step, that is, an interrogation of all the units 11, whether the last analysis step has been completed, can be omitted from the print-out command program of the control unit C.

The main path 1 and the test and treatment or analysis path 2, and the associated conveyor systems are preferably located in parallel to each other. This arrangement reduces the size and particularly the height of the analysis apparatus and permits construction in an easily supervised and clear manner. The lengths of transport or conveyor systems can be matched to each other. The transport or conveyor systems may be of different types. The main conveyor path 1, preferably, is an endless, discontinuously moving transport ribgon or web, on which a sample receptacle 8 is placed until it meets the switch 3, where switch 3 arrests either the moving web and holds on the sample receptacle. If a test quantity has been removed by the transfer device 4, the web is energized to move the sample container 8 to the next switch 3 of the next unit 11, where the cycle will repeat. The conveyor for the test and treatment transport path 2 preferably operates in steps; the containers are placed in a holder 13 (FIGS. 2, 4) which contains a series of reactants, cuvettes, test tubes, or the like containers, for respective treatment of a test sample removed from the sample receptacle 8, and testing physical and/or chemical characteristics thereof, before or after treatment, or reaction with reagents. Stepped movement of the containers 12 is, preferably, provided by engagement of the containers 12 with a positive drive chain operating in discrete steps. The holder 13 for the test and treatment containers 12 may be moved as an entirety through its path, for example by a rack-and-pinion drive, a Geneva movement, or the like. One holder 13 may follow the next and drive may be effected only on one holder, one holder pushing the preceding one through the test and treatment path 2. During analysis of a test sample in container 12 of holder 13 through the test and treatment path 2, therefore, a sample receptacle 8 passes through the main path 1 from the sample feeder 5, through a modular unit 11 and is then received in the collecting box 6 for used sample receptacles after passing all modular units 11 if more than one unit is used where it can be removed for washing and re-use, or can be discarded, or for automatic cleaning and recycling. In contrast to this movement of the main sample receptacle 8, the test and treatment containers 12 which contain reagents or which are subjected, with test sample quantities of the fluid to be checked, to various testing analysis and/or treatment steps, move only through the test and treatment path of a single unit or module 11. Preferably, these containers 12 are assembled together in a holder 13. Each unit or module 11, therefore, has a main path or track 1 and a test and treatment path or track 2, a control switch 3 and a transfer device 4. The main path, track or conveyor for each one of the modules forms a portion of the overall main movement path of the sample receptacles 8.

Figure 2:
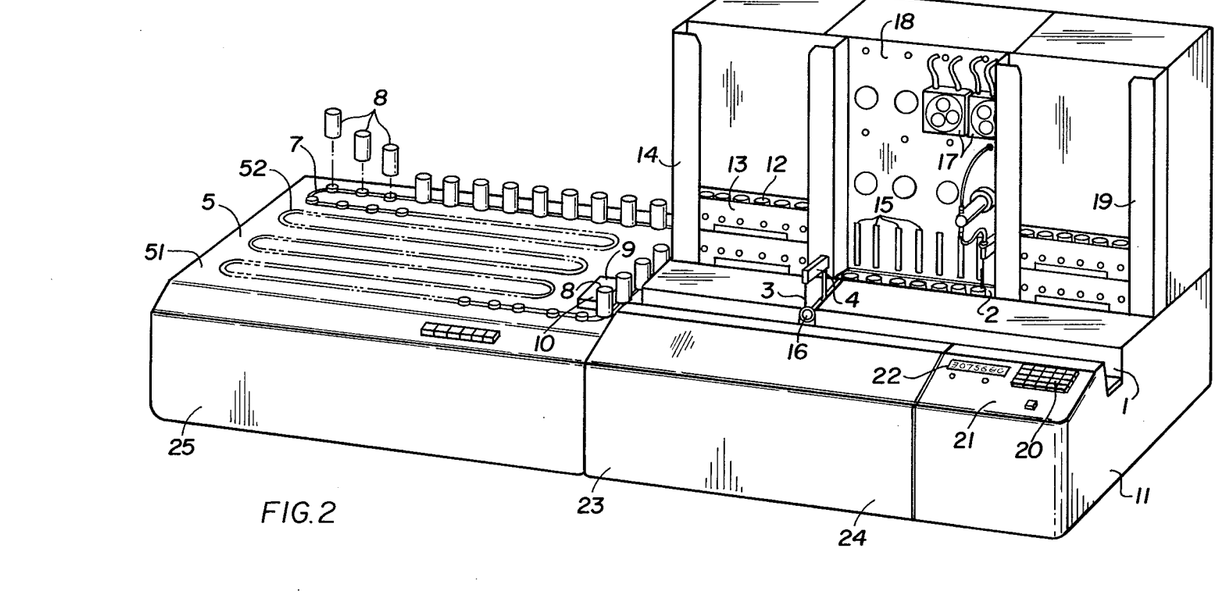
FIG. 2 is a schematic front view of the feeding station and a first one of a chemical apparatus unit, to which further similar apparatus units can be added, and showing the main elements thereof.

FIG. 2 illustrates in greater detail only the first one of the modules 11; these modules 11 may be combined in any suitable form to carry out various chemical and physical tests and analyses. For illustration, a holder 13 is shown in which seven test and treatment containers are in the test and treatment path 2, associated with respective testing, treatment, and analysis stations 15, of which seven are shown in FIG. 1. These stations 15 are equally spaced from each other and can be associated with the respective containers 12 upon stepped movement thereof in path 2, preferably in a direction parallel to the main path or track 1.

In a preferred embodiment, and as shown in FIG. 1, the sample receptacles 8 move in the main path from switch 3 to switch 3 of each modular unit. The test and treatment cycling time of th test and treatment containers 12 is determined by the duration of the longest analysis step at any one of the analysis stations 15. Upon expiration of this analysis cycling time, any one of the containers 12 is moved in the path 2 from one treatment station 15 to the next. The dwell time during the movement of the containers 12 will be determined by the nature of the longest analysis, the test, or the treatment being carried out on the sample within the container 12. Movement to a next analysis, test or treatment position 15 will be effected only after the longest one of the time periods, that is, the cycling time of the stepping in path 2 has elapsed. This cycling time, preferably, is the same in all the analysis modules 11, of which four are shown by way of example in FIG. 1.

If the particular sample material in the receptacle 8 requires only a single analysis then, of course, only a single module or unit 11 is needed between the feeding unit 5 and the used receptacle receiver 6.

Figure 3:
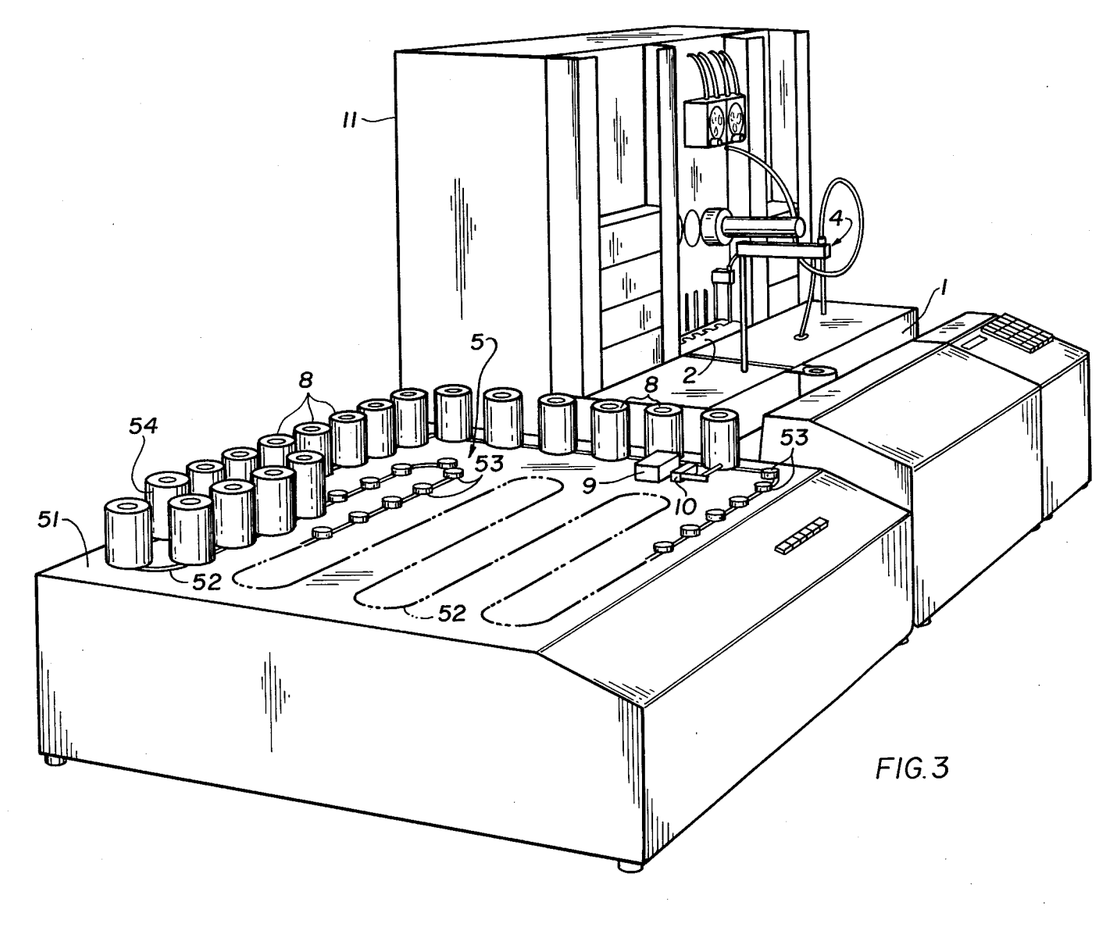
FIG. 3 is a perspective view of the feeding unit, the sample receptacle injection apparatus and, in schematic form, a first one of the chemical analysis units.
Figure 4:
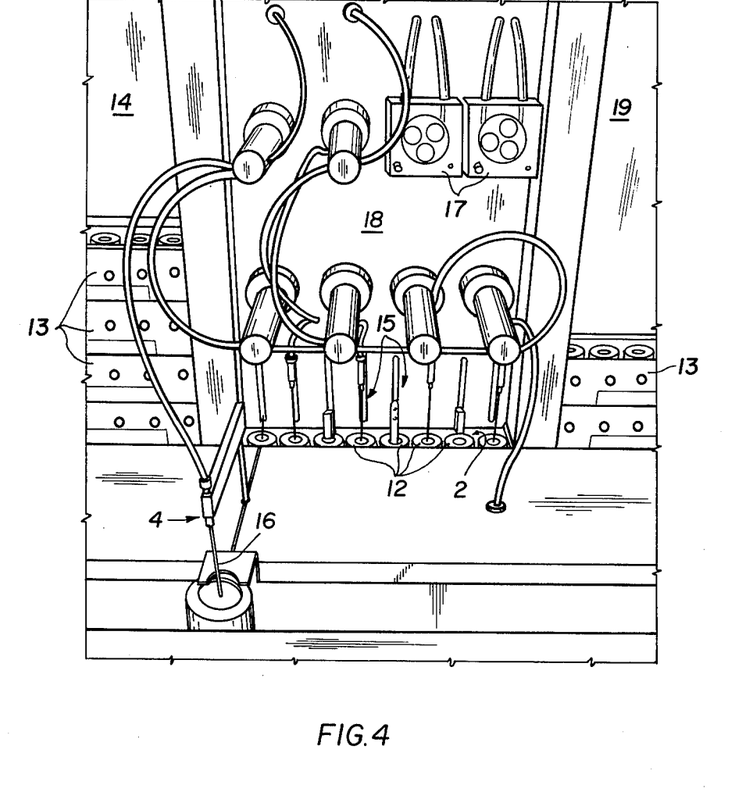
FIG. 4 is a schematic isometric fragmentary view of one chemical analysis unit, the transfer station, and showing the main and testing and analysis paths.

Referring specifically to FIGS. 2–4: The analysis units or modules 11 are formed with U-shaped hoppers, a transport path 2, beneath which, for example, a discontinuously moving or stepped belt is located. The containers 12 are located in magazines or holders 13 which are stacked in a supply stack 14 having an open end to place therein as many holders as the height of the apparatus will allow. The holders are then removed laterally, one-by-one, permitting the magazines 13 to drop downwardly. They are moved horizontally to the various analysis stations 15. The first one of the analysis stations is associated with a transfer apparatus 16, forming a portion of the transfer station 4, and in which a sample is removed from the sample receptacle 8 to be introduced into one of the test and treatment containers 12. A suitable apparatus for the sample transfer device is described in U.S. application Ser. 617,999, by co-inventor Koukol hereof, filed Sept. 30, 1975, and assigned to the assignee of the present application.

Depending on the nature of the station 15, various types of treatment, analyses, or tests can be carried out, for example: Measuring of the quantity introduced; stirring; filtration; degassing; thinning with a solvent; incubation, or the like. The necessary apparatus such as pipettes, stirrers, filters, heaters, or pumps, of which two peristaltic pumps 17 are shown in FIGS. 2 and 4, and th like, are all secured to a vertical support plate 18. Support plate 18 holds the various elements of station 15 at uniform spacing from each other, which corresponds to the spacing of the test and treatment containers 12 from each other within the holders 13 and also to the stepped length or distance of the conveyor of path 2. Pipettes, canulas, burettes, and other test and sensing devices, and connected to suitable physical and chemical detectors, are likewise secured to plate 18, and spaced equally from each other, and forming part of the respective stations 15.

Detectors which may be used in the modular units 11 may, for example, automatically determine the density of a liquid as illustrated, for example, in U.S. Pat. No.

3,523,446. Refractometers may be used for automatic determining of refraction indices, or the like. An automatic titration burette may be used for potentiometric titration to a predetermined end point, for example to determine the acidity of a liquid.

Albumen in the liquid can be determined, for example, by analysis with a photometric apparatus as a detector, as well known. Other determinations may be made, for example enzymatic substrate determination for enzymes bound to a carrier, for example glucose, fructose, or alcohol content of the liquid. A filter photometer may be used as a detector to evaluate the test results.

The test samples are placed in sample receptacles 8 which are then loaded on the sample feeding unit 5 (FIGS. 2, 3). These sample feeders 5 are cup-shaped elements 54, open at the top but closed off by a cover capable of being pierced by a syringe needle. The bottom of the cup-shaped elements 54 is formed with a recess of such size that it fits over and matches projecting buttons 53 which project from the top plate 51 of the feeder 5. The top plate 51 is formed with a meandering or sinuous notch below which a suitable drive chain is located to which buttons 53 are attached. The receptacles 8 are provided with suitable labels indicating the contents placed therein. The labels, which may be affixed in machine-readable form such as OCR (optical character recognition) characters, or in magnetic form, are moved along the sinuous path and then past a sample identification reader 9 to then be placed adjacent a sample injecting device 10. At the position of injector 10, the button 53 can be retracted and, upon command from the control unit C (FIG. 1), that a new sample receptacle 8 is to be introduced to path 1, a magnetically operated pusher rod pushes the next sample receptacle 8 on path 1. At the same time, the previously read sample identification, as read by reader 9, is stored in control unit C for allocation, upon print-out, with the test results.

The same feeder 5 stores the containers 54 forming the receptacles 8, and can be re-filled with new containers 8, as desired. The labels applied thereto can be permanently affixed or removable; it is not necessary, however, to provide for automatic symbol reading since data regarding the particular sample to be tested can also be inserted manually. Since only a single receptacle 8 is in the main path 1 at any one time during the period of time that the test and treatment containers 12 are in the test and treatment path 2 and are being analyzed, it is sufficient if the main sample receptacle 8 has a number associated therewith which is introduced, manually or automatically, for storage in a control unit C, or in a computer print-out terminal for association with the analysis results as obtained by the various analysis apparatus and tests being carried out by units 15.

The use of moving buttons in a meandering track on which sample containers can be placed, which sample containers are formed with similar indentations, provides a simple apparatus which is reliable, easily maintained, checked and cleaned, while permitting the utmost in versatility and storage capacity so that a large number of sample receptacles 8 can be placed thereon, for subsequent automatic analysis, without further human attention thereto.

Example of a typical analysis: Determination of density of wine: Feeder 5 is supplied with sample receptacles 8, each one carrying a number code, by placing the receptacles 8 on the projecting buttons 53. The receptacles 8 are closed off at the top in gas-tight manner in such a way that the cover can be penetrated by a hypodermic needle forming part of the transfer device 16. The transport path 7 (FIG. 2) of the feeder 5 is sinuous; the feeder 5 can be charged with the various receptacles 8 at any suitable time. Additional receptacles 8 may be placed on empty positions of the feeder 5 of the analysis apparatus, as empty positions arise, even after analysis of the first samples has commenced.

The test and treatment containers 12 are inserted in the respective holders 13 and the holders are then placed in the stack feeder 14. The containers 12, before use, may be empty and are closed with a cover capable of being perforated by a hypodermic needle. so as to be gas-tight; they may, if desired, and if the analysis so requires, contain measured quantites of reagents in liquid or other form. Carriers 13, filled with test and treatment containers 12, and then introduced into the feeding rack 14 from the top until the rack 14 is completely filled with superimposed stacked holders 13. The containers 12 in holders 13, as well as the receptacles 8 in the feed path 7 of feeder 5 now are ready for further movement and the apparatus can be started.

The start button on a control panel 21 on each one of the modules, or an override start button on the control unit C, is then operated; the control panels 21 of the modules themselves are preferably so arranged that they can be operated in tandem, similar to modular expansion of PBX switchboards, or multiple train controls, so that operation of any one of the start buttons of any one of the modules will start the entire apparatus. The program for the respective analysis then begins. This program can be determined by a numerical control program stored, for example, on magnetic tape, punched tape or the like, or by an internal programmed memory.

Upon commencement of operations, a first magazine 13 is laterally moved from stack 14 to the test and treatment path 2, and shifted so that the first one of the containers 12 will be at the first position 15, corresponding to charging thereof by the charge station 4. Simultaneously, a receptacle 8 is identified and pushed by means of pusher 10 on the feeder 5 to the transport conveyor of the main path 1, which starts or has been started, and transports the first receptacle 8 until it reaches switch 3. At that point, the transport conveyor is stopped and transfer device 16 in station 4 is energized. A predetermined quantity, for example 5 milli-liters, of wine are removed from receptacle 8 and transferred to the first one treatment container 12, which is now in the first position of the test and treatment path 2. The transport conveyor of the main path 1 is again energized and receptacle 8 is transported to the next modular unit 11 until it again reaches switch 3 of the next modular unit.

After expiration of the cycling time, the pusher 10 of the feeder 5 moves a further receptacle 8 on the main path 1. The further receptacle 8 will again stop as soon as it reaches switch 3. The holder 13, together with the test and treatment containers 12, will step by one step, the transfer apparatus 16 starts and transfers the predetermined quantity of wine to the second test and treatment container 12 in the holder 13. The first test and treatment container 12 is now on the second treatment station 15. This treatment station includes a degassing device. As soon as the treatment station is occupied by a test and treatment container 12, for example as scanned photoelectrically, or as sensed mechanically by a microswitch, the de-gassing apparatus is started and the quantity of wine within the first test and treatment container 12 is de-gassed for a predetermined time period, as determined by the particular testing program, for example for 150 seconds.

After expiration of the cycling time, which may be longer than 150 seconds, the third sample receptacle 8 is placed on the main path 1 where, after it reaches switch 3, a sample is introduced by transfer device 16 in the next test and treatment container 12 in holder 13. At the same time, the second container 12 has now been moved to the second analysis station 15 and the first container 12 has moved to the third analysis station 15.

In similar manner, the analysis containers 12, limited only by the length of the holder 13, are moved through the various treatment stations 15 along the test and treatment path 2, to be treated or tested in various ways. The last station, for example, carries out the final measuring or analysis. At this station, the quantity of wine in the container 12 is filtered and transported by means of the peristaltic pump in a measuring cell. The peristaltic pump is connected to an automatically operated syringe which penetrates the cover of the container 12 to remove liquid therefrom. The wind, previously treated in the various treatment stations 15, is first raised to a suitable temperature; thereafter, its density is measured three times with an interrupting gap of 5 seconds therebetween. The data so derived are transferred to a compiler, memory, or similar storage element, for example in a computer. The computer now computes its program to calculate the density from the measured results and prints out or displays the results for the first sample contained in the first sample receptacle. After a further cycling period, the sample previously tested in the various steps and contained in the second one of the sample receptacles will arrive at the final testing station, and the density is measured in similar manner.

All the measuring and analysis results for a specific sample in a specific receptacle will thus arise within one cycling time. This principle of maintaining the same cycling time on the main path 1 and on the test and treatment path 2 deos not change if different methods of analysis are used, or if different determinations are made or other liquids are used. The cycling time always remains the same, and will be that one with the longest duration of the analysis or testing steps.

The test and treatment steps in any one of the units 11 can be separately printed out or displayed with respect to the unit, and with respect to the respective sample receptacle, and stored for consolidated read-out or print-out after the analyses and tests of that specific sample have been carried out in all the modular units 11. At that time, the computer presents an interrogation signal, coded with respect to the specific coding of the specific sample receptacle (e.g. No. 1) from which the samples were analyzed, for subsequent display or print-out on a single analysis result in which the analyses of all the various units 11 are consolidated.

The test and treatment containers 12 in the holders 13 are transferred to a magazine hopper 19 for removal. The containers 12 may be so constructed that they are disposable, that is, used only once; or that they are re-usuable so that, after cleaning and refilling in the magazine holders 13, they can be reintroduced into the rack 14. Transport through the rack 14 and hopper 19 is in vertical direction, in steps, and in such a manner that each time a holder 13 is laterally shifted, a holder in the units 14, 19 is moved in vertical direction.

Each one of the modular units 11 includes an operating console 20 in which the program for the analysis steps to be carried out can be entered. Preferably, each one of the control panels 21 also is provided with an indicator or digital display 22 to indicate or display the code number or the particular receptacle 8 whose contents are then being analyzed. Each modular unit 11 additionally includes space 23 for storage or reagents as well as receptacles 24 for used reagent, or for already used containers 12 which are to be disposed of. The receptacles 8 may be made to be disposable, after test and analysis of their content is terminated, or they can be made for re-use after washing and re-filling, and replacement on the path 7, that is, on buttons 53 of the feed unit 5. Preferably, the feed unit 5 is also provided with an electric programmer 25 (FIG. 2) which may contain the controller C (FIG. 1) to automatically control the desired analysis operations of the modular units 11, as well as, if desired, electronic data processing of the data derived upon analysis which, together with the code number of the sample in the respective receptacle 8, can then be transmitted to a printer of similar display unit (not shown).

Figure 5:
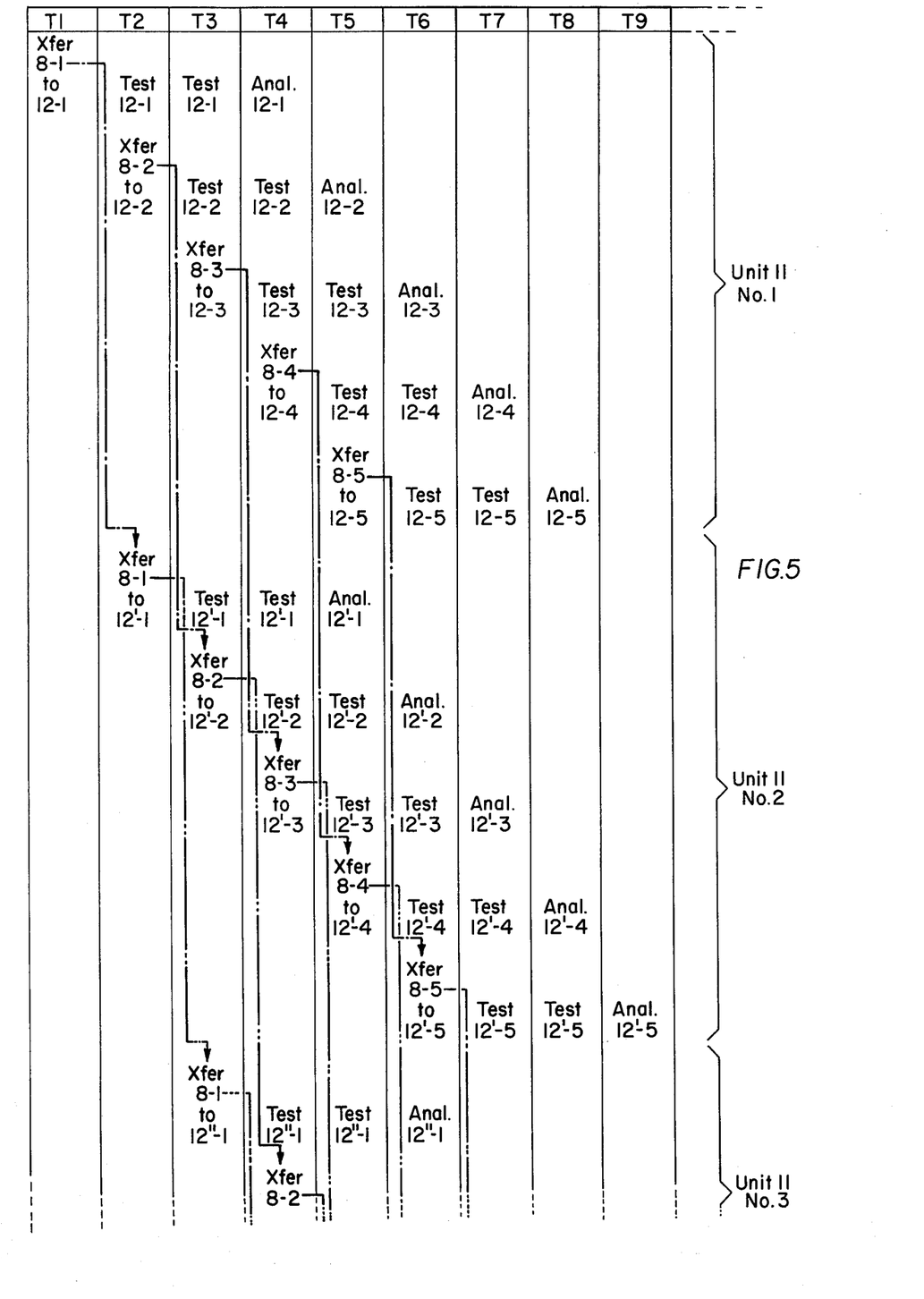
FIG. 5 is a schematic timing diagram showing movement of receptacles and containers.

FIG. 5 illustrates a timing diagram in connection with one embodiment of the invention. The following notation has been used: 8-1 is the first receptacle 8 being introduced into the main path 1, and coded 1; 8-2 is the second receptacle 8 coded 2, etc.; the test containers are likewise numbered 12-1, for the first test container, and so on. The example of FIG. 5 illustrates two test steps and one analysis step. The prime and double prime notations have been used for succeeding units 11 which are operated in tandem (of which four are shown in FIG. 1) each having three stations 15, two for testing and one for analysis.

As is clearly apparent from the diagram, at any one time slot or time window indicated at T1, T2 . . . T9, only one container 8 will be at the transfer position, that is in path 1 of any one unit. While, in any unit, the transfer operation from receptacle 1 to container 12 takes place, the previously transferred sample from a previous receptacle 8 is being analyzed at the analysis station during that then occurring time slot or time window. Since all time slots or time windows are the same, allocation of the appropriate output from the units to the appropriate sample being analyzed is simple. The time periods T1 . . . T9 thus represent clock periods of operation, whether the entire period of time is needed for a specific testing, analysis or treatment step, or not. The time taken to transfer a receptacle 8 from one unit to the next is small and can be accommodated within the same time slot, as indicated by the transfer lines.

Various changes and modifications may be made within the inventive concept.

We claim:

1. Automatic chemical analysis apparatus unit for repetitively carrying out different analyses and testing steps of substances located in sample receptacles (8) comprising
   a main sample receptacle transport conveyor (1) holding and moving sample receptacles (8) along a main transport path;
   a plurality of test and treatment containers (12), and a test and treatment transport conveyor (2) holding and moving the test and treatment containers (12) along a treatment transport path;
   a test and treatment sampling transfer station (4) including test and treatment transfer means (16) located adjacent both said paths and transferring a test and treatment sampling quantity of substance from the sample receptacle (8) to one of the test and treatment containers (12);

a plurality of testing and treatment stations (15) located adjacent said test and treatment path (2) to effect treatment of and analysis and testing of the sampling quantity in the test and treatment containers (12) as they are moved along the treatment transport path;

and control means (C, 25) coupled to the test and treatment transport conveyor (2) controlling, in steps, a. movement of said test and treatment containers (12) past said plurality of testing and treatment stations (15), and b. the dwell time of said test and treatment containers at said stations, all the test and treatment containers (12) moving at the same speed and having the same dwell time at each station, said dwell time being the time required by the longest of the treatment, analysis or testing steps respectively carried out at said stations.

2. Apparatus unit according to claim 1, wherein the main transport path of the main transport conveyor and the treatment transport path of the test and treatment transport conveyor are parallel.

3. Apparatus unit according to claim 1, wherein the control means (C, 25) additionally controls introduction of further sample receptacles (8) to the sample receptacle transport conveyor (1) and hence to the main transport path only at a time being determined by the slowest time of analysis or testing steps of any one of the apparatus units (11), and provides a cycling time for sequential introduction of sample receptacles (8) to said main transport path which is equal to the dwell time of said test and treatment containers (12) in the test and treatment path (2) to permit unambiquous correlation of the test and treatment results in the test and treatment path to a respective sample receptacle (8) on said main transport path.

4. Multi-analysis automatic analysis apparatus comprising at least two apparatus units as claimed in claim 1 wherein said control means (C, 25) is common to both said units (1) and control the movement of c. the sample receptacles (8) in said main transport track (1), and d. the movement of the test and treatment containers (12) in the respective test and treatment transport paths (2) of the respective units (11)

to be in the same steps, and with the same dwell time.

5. Apparatus according to claim 4, wherein the movement of said test and treatment containers (12) is controlled to occur in accordance with the slowest one of any of the analysis and testing steps in any one of the at least two apparatus units.

6. Apparatus according to claim 4, wherein said apparatus units are modular units; the main transport paths (1) of said modular units (11) being in alignment, for successive transport of said sample receptacles (8);

a control switch (3) is provided, located adjacent the transport conveyor of each of the modular units (11) and controlling the respective test and treatment transfer means (16) of the respective modular unit (11) when a sample receptacle is transported thereto, and stopping the main transport conveyor when a sample receptacle (8) meets control switch (3).

7. Apparatus unit as claimed in claim 1, further including a sample receptacle feed unit (5) comprising a support plate (51) having a track (52) formed thereon to move the sample receptacles (8) along a supply path (7);

transport conveyor means including buttons (53) projecting from said tract (52) and located in said path;

and wherein the receptacles (8) comprise a partly hollow cup-shaped body (52) formed with a recess at the bottom thereof matching and engageable with said projecting buttons (53) for removable engagement therewith and movement along said supply path (7).

8. Apparatus unit as claimed in claim 7, wherein the control means (C, 25) synchronize movement of sample receptacles (8) with movement of the test and treatment conveyors (12) past the plurality of testing and treatment stations (15) by means of control switch (3).

9. Apparatus unit as claimed in claim 7, further comprising an identification station (9) located in sensing relation to the sample receptacles (8) in said supply path (7);

and a sample injection means (10) to remove a single receptacle (8) from the button and introduce it into the main transport track (1), the sample identification station (9), the injection means (10) and the test and treatment transport conveyor (2) being connected to said control means (C, 25) to control introduction, so that only one sample receptacle (8) will be on the main transport track (1) at any one time.

10. Multi-analysis automatic analysis apparatus as claimed in claim 4, further comprising a sample receptacle feeder unit (5) having means (52, 53) to move the sample receptacles (8) along a feed supply path (7);

an identification station (9) located in sensing relation to the sample receptacles (8) in said supply path (7);

a sample injection means (10) to remove a sample receptacle (8) from the receptacle moving means and introduce it into the main transport path (1);

the sample identification station (9), the injection means (10), the test and treatment transport conveyors of the respective units (11) being connected to said control means (C, 25) to synchronize movement of a sample receptacle (8) with movement of the test and treatment conveyors (12) past the plurality of testing and treatment stations (15) of the respective apparatus units (11) and permit introduction of a receptacle (8) to the test and treatment transfer station (4) and initiates a control swtich (3) of any one unit so that only one sample receptacle (8) will be in the treatment path (1) at any one time.

11. Apparatus according to claim 10, wherein the control means synchronizes introduction of the sample receptacles (8) so that any sample receptacle will be in the main path (1) of any one respective unit (11) at any one time.

12. Apparatus according to claim 10 or claim 11, wherein the control of movement of the test and treatment containers (12) from one station to the next being so that final evaluation of test data of a sample at all of the analysis apparatus units (11) will occur at the same time so that said test data can be allocated only to one sample in a sample receptacle (8).

13. Apparatus according to claim 10, 11, or 12, wherein the test data of any one of the samples is stored in an electronic data processor of a computer together with sample identification code and that all test results of all units (11) are evaluated at the same time when the computer presents an interrogation signal for display or print-out.

14. Method to automatically carry out analysis operations, repetitively, on different test samples, comprising the steps of;
   moving a main sample receptacle (8) along a main transport path (1);
   moving a plurality of test and treatment containers (12) in a test and treatment path (2);
   Transferring a sample of the material to be analyzed from the main sample receptacle (8) to one of the test and treatment containers (12) at a predetermined instant of time;
   and controlling the movement of the test and treatment containers, in discrete steps, past a plurality of analysis, treatment and sensing stations (15), wherein the movement steps are all equal and correspond to at least the longest one of the analysis, treatment or sensing steps at said stations (12),
   and inhibiting movement of a further sample receptacle (8) to appear along said main transport path until, at least, one of said movement steps of the treatment containers (12) in the treatment transport path (2) from one analysis, treatment or sensing station (15) to the next has occured, so that the stepping time of movement of all said test and treatment containers (12) will be equal.
   so that only one sample receptacle will be in the main transport path (1), and allocation of analysis, treatment and test steps with the material taken from any one of the sample receptacles will be unambiguous and determined by a time slot, or timing window, which progresses, in steps, with the stepping movement of the test and treatment container (12) along said test and treatment path (2).

15. Method according to claim 14, wherein a plurality of apparatus units, each including a plurality of testing and treatment stations (15) are provided, each having a separate main transport path and a separate treatment transport path;
   and wherein said method further comprises moving the test and treatment containers (12) of the individual units (11), in steps, all at the same stepping rate;
   and moving a sample receptacle (8) after the test and treatment sampling of any one unit to effect the test and treatment sampling transfer at a subsequent unit in the same time as a moving step of the test and treatment containers (12) so that the analysis, treatment and sensing results in sequential units will appear in sequential time slots, or timing windows.

* * * * *